US007376451B2

(12) United States Patent
Mahony et al.

(10) Patent No.: US 7,376,451 B2
(45) Date of Patent: May 20, 2008

(54) MEASUREMENT AND TREATMENT SYSTEM AND METHOD

(75) Inventors: Michael Joseph Mahony, Schenectady, NY (US); John Erik Hershey, Ballston Lake, NY (US); Glenn Alan Forman, Niskayuna, NY (US); Harold Woodruff Tomlinson, Jr., Scotia, NY (US); William Eugene Powell, III, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 161 days.

(21) Appl. No.: 10/973,598

(22) Filed: Oct. 27, 2004

(65) Prior Publication Data

US 2006/0089546 A1    Apr. 27, 2006

(51) Int. Cl.
*A61B 5/1455* (2006.01)
*A61B 5/00* (2006.01)
(52) U.S. Cl. ...................... 600/310; 600/323
(58) Field of Classification Search ............... 600/310, 600/322, 323, 344
See application file for complete search history.

(56) References Cited

U.S. PATENT DOCUMENTS

| | | | | | |
|---|---|---|---|---|---|
| 3,463,142 | A | * | 8/1969 | Harte | 600/314 |
| 4,895,155 | A | * | 1/1990 | Lee | 600/324 |
| 5,313,941 | A | * | 5/1994 | Braig et al. | 600/322 |
| 5,339,223 | A | * | 8/1994 | Kremenchugsky et al. | 606/16 |
| 5,978,691 | A | * | 11/1999 | Mills | 600/334 |
| 5,995,856 | A | * | 11/1999 | Mannheimer et al. | 600/323 |
| 6,070,093 | A | * | 5/2000 | Oosta et al. | 600/316 |
| 6,088,605 | A | * | 7/2000 | Griffith et al. | 600/316 |
| 6,470,200 | B2 | | 10/2002 | Walker et al. | |
| 6,526,298 | B1 | * | 2/2003 | Khalil et al. | 600/310 |
| 6,596,016 | B1 | * | 7/2003 | Vreman et al. | 600/310 |
| 6,611,320 | B1 | * | 8/2003 | Lindberg et al. | 356/40 |
| 6,635,491 | B1 | * | 10/2003 | Khalil et al. | 436/95 |
| 2003/0189363 | A1 | * | 10/2003 | Artsvelyan | 297/227 |

OTHER PUBLICATIONS

"Noninvasive Optical Method of Measuring Tissue and Arterial Saturation: An Application to Absolute Pulse Oximetry of the Brain", Maria A. Franceschini, E. Gratton and S. Fantini, Optical Society of America (1999)—pp. 829-831.

* cited by examiner

*Primary Examiner*—Eric F Winakur
(74) *Attorney, Agent, or Firm*—Jenifer E. Haeckl; Jason K. Klindtworth (57) ABSTRACT

A non-intrusive physiological data measurement system and method, as well as an optically induced treatment system, are described. The measurement system includes a monitoring mechanism that includes light emitter modules capable of emitting light at at least two wavelengths. The light emitted from the light emitter modules is transmitted through a subject and to a light receiving mechanism, such as an optical sensor. Physiological data is taken from the received light. The system also can ascertain movement of the subject by obtaining an initial outline of the subject and comparing that outline with a subsequently obtained outline. A therapeutic optic system includes a non-adhering light emitting mechanism for providing light at therapeutic wavelengths.

20 Claims, 6 Drawing Sheets

MEASUREMENT AND TREATMENT SYSTEM AND METHOD

BACKGROUND

The invention relates generally to a system and method for obtaining physiological data measurements and providing certain optically induced treatment regimens, and more particularly to a system and method for optically measuring oximetric information and providing photodynamic therapy or tissue healing therapy through non-intrusive means.

There are numerous instances where oximetric measurements are necessary for the proper treatment of individuals experiencing some form of health crisis. For example, neonates, newborn babies with a birth weight of 1500 grams or less, are in a fragile state immediately after birth and for some time thereafter. Due to their fragility, any disturbance to them could be dangerous, and even life threatening. Neonates must be continually and extensively monitored so that the most efficacious medical regimen may be administered. Most physiological monitoring mechanisms incorporate extensive sensors and cabling which must be attached to the neonate, and such monitoring mechanisms lead to a tension between the need to monitor neonates and the need to disturb them as little as possible.

Figure 1:
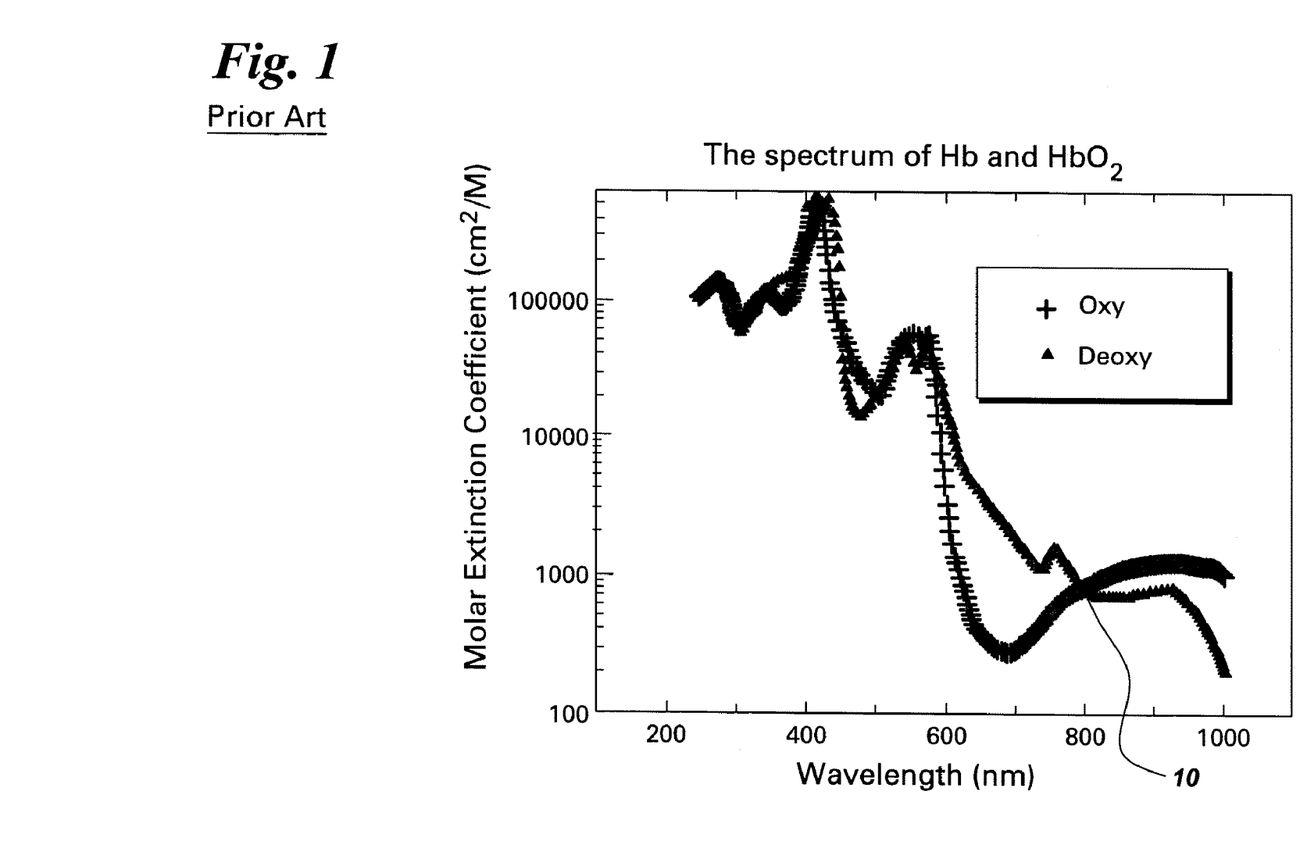
FIG. 1 illustrates an isosbestic wavelength point at about 805 nanometers.

Two important measurements for neonates include detection of physical movement as a sign of life and estimation of cardiac and cardiopulmonary data, including pulse oximetry. Conventionally, pulse oximetry is often performed through an oximeter which is attached either at the finger or the ear and which measures the absorption of light of two different wavelengths. A pulse oximeter works by passing a beam of red and infrared light through a pulsating capillary bed. The ratio of red to infrared blood light transmitted gives a measure of the oxygen saturation of the blood. The measurements of the two different beams, which have two different wavelengths, usually straddle an isosbestic point, the wavelength at which the molar extinction coefficients are equal, i.e., the point at which the absorption spectra of two species cross each other. As shown in FIG. 1, the two species are oxyhemoglobin ("Oxy") and deoxyhemoglobin ("Deoxy"), and their molar extinction coefficients are equal, namely the isosbestic point 10, at a wavelength of about 805 nanometers. For neonates, use of a finger or ear oximeter for obtaining pulse oximetry is disturbing.

Another conventional approach for obtaining pulse oximetry is found in U.S. Pat. No. 6,470,200, in which is disclosed a pacifier with an oximetric sensor. The sensor may be optionally equipped with wireless communications, for wirelessly reporting the measured oximetric data. This approach is not suitable for neonates, as they are not yet developed fully to the stage of being able to reliably handle a pacifier.

Another example of when oximetric monitoring is important is during a surgical procedure under a general anesthetic. Conventional anesthetic mechanisms are closed systems that re-circulate the anesthetic. Known anesthetic mechanisms utilize a canister that includes a carbon dioxide scrubber through which the expired outflow from the patient, including the anesthetic and expired air, is recycled. The carbon dioxide scrubber removes the carbon dioxide from the outflow. One known anesthetic mechanism uses Baralyme® as the scrubbing material and Sevoflurane™ as the anesthetic. Carbon dioxide scrubbers have an initial level of moisture, and through use become less moist. If a carbon dioxide scrubber becomes desiccated, a build up of carbon monoxide may occur in the scrubber, and that carbon monoxide may be added to the outflow. Carbon monoxide has an affinity for hemoglobin that is more than two hundred times greater than that for either oxygen or carbon dioxide, and the introduction of carbon monoxide in the outflow can lead to carboxyhemoglobin in levels that are dangerous to the patient.

Additionally, there are certain medical treatment regimens that are optically induced, namely that utilize light in a somewhat catalytic way. For example, light may be used to activate light-sensitive chemotherapy drugs. Also, light may be used to stimulate tissue growth and regeneration.

There exists a need for an efficacious methodology for gathering physiological data and for performing certain optically induced treatment regimens that is less disturbing to the patient.

SUMMARY

The present invention describes a system and a method for obtaining physiological data measurements and for optically inducing therapeutic treatment.

One exemplary embodiment of the invention is a physiological data measurement system that includes a non-adhering signal emitting mechanism and a signal receiving mechanism. The signal emitting mechanism includes a monitoring mechanism configured to monitor physiological data of and provide support to a subject and at least one signal emitter module within the monitoring mechanism. The signal receiving mechanism is configured to receive signals emitted from the at least one signal emitter module.

Another exemplary embodiment of the invention is a treatment system that includes a non-adhering light emitting mechanism. The non-adhering light emitting mechanism includes an optical treatment array mechanism configured to provide optical treatment to and provide support for a subject and at least one light emitter module within the optical treatment array. The at least one light emitter module is configured to emit a light at a therapeutic wavelength.

Another exemplary embodiment of the invention is an incubating system that includes an incubator and a non-adhering physiological data measurement system configured to measure physiological data of and provide support to a subject.

One aspect of the incubating system embodiment includes a light emitting mechanism and a light receiving mechanism. The light emitting mechanism includes a monitoring pad configured to monitor physiological data of and provide support for a subject, and a single light emitter module within the monitoring pad and including a broadband light source. The light receiving mechanism is configured to receive light emitted from the broadband light source.

Another exemplary embodiment of the invention is a light emitting mechanism for use in a physiological data measurement device. The light emitting mechanism includes a non-adhering monitoring mechanism configured to measure physiological data of and provide support for a subject, and one or more light emitter modules within the monitoring mechanism, each of the light emitter modules being configured to emit light at at least two wavelengths.

Another exemplary embodiment of the invention is a method for obtaining physiological data measurements. The method includes determining an outline of a subject through a sequential transmission of light from a plurality of light emitter modules, sequentially turning on and off individual ones of the plurality of light emitter modules that are within the outline of the subject, and collecting data and estimating physiological data values.

Another exemplary embodiment of the invention is a method for ascertaining movement of a neonatal infant being monitored. The method includes determining an outline of a neonatal infant through a sequential transmission of light from a plurality of light emitter modules, collecting initial data on the initial outline of the neonatal infant, and then, re-determining a subsequent outline of the neonatal infant through another sequential transmission of light from the plurality of light emitter modules to ascertain whether the subsequent outline differs from the initial outline.

These and other advantages and features will be more readily understood from the following detailed description of preferred embodiments of the invention that is provided in connection with the accompanying drawings.

DETAILED DESCRIPTION OF EXEMPLARY EMBODIMENTS

Embodiments of the invention described herein relate to a monitoring and/or treatment system utilizing a non-adhering interrogation mechanism. The non-adhering interrogation mechanism may employ optical spectra and/or electromagnetic field data to obtain physiological data measurements from a subject in a non-adhering way. By non-adhering is meant that physical adherence of sensors to the skin of a subject is not required to obtain physiological data measurements. Adhering sensors include those utilizing an adhesive of some sort to attach the sensor to a subject and those known finger and ear pulse oximeters which utilize a clamping force on the subject to retain attachment of the sensor.

Figure 2:
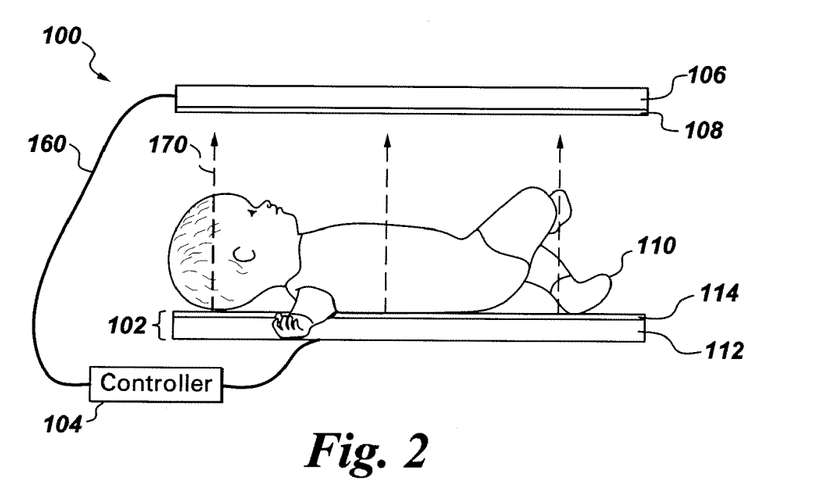
FIG. 2 is a schematic view of a physiological data measurement system constructed in accordance with an embodiment of the invention.
Figure 4:
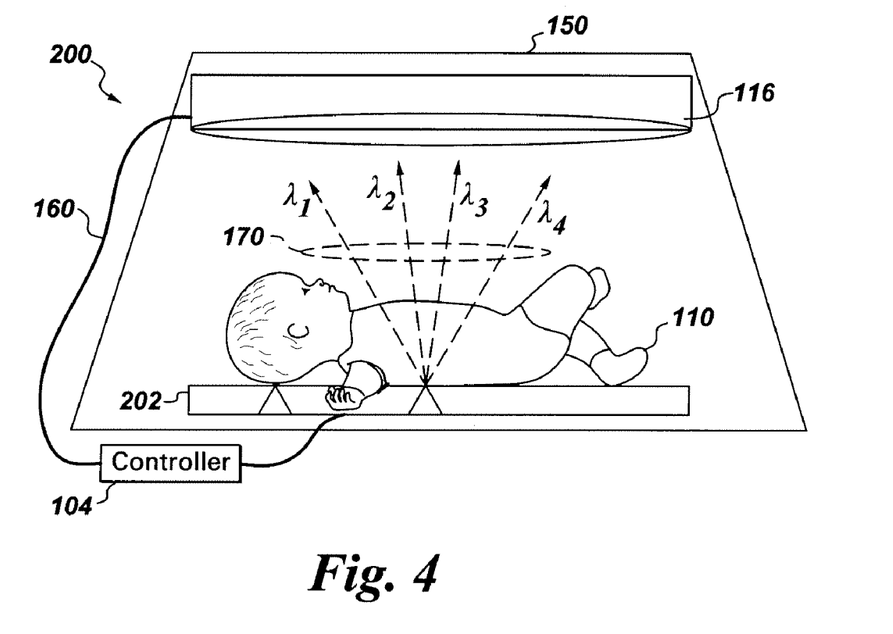
FIG. 4 is a schematic view of a physiological data measurement system constructed in accordance with an embodiment of the invention.

Referring now to FIG. 2, there is illustrated an embodiment of the monitoring system, namely a physiological data measurement system 100 that includes a monitoring mechanism 102, a controller 104, a light-sensing array 106, and a lens 108. Provided the light-sensing array 106 is sufficiently large, the lens 108 may be optional. The measurement system 100 may be used for obtaining, for example, oximetric data from a variety of high-risk patients 110. One example of a high-risk patient 110 are neonatal infants or neonates, in which case the measurement system 100 may be incorporated within an incubator 150 (FIG. 4).

The monitoring mechanism 102 may include a pad formed of a suitable fabric-like material. Since the subject patient 110 may lie on the monitoring pad 102, the pad (and any underlying structure) should be able to sustain the patient's weight while also providing support and comfort to the patient.

Within the monitoring pad 102 is a single light emitter module 112. The light emitter module 112 is preferably a broadband light source, and it may include solid state optoelectronics, such as a surface emission laser diode, that can be made to consume low levels of power, provide single-mode or multi-mode light, and be controlled by mechanical (MEMS) or electrical means to provide optical emission for a tunable spectrum of light.

The measurement system 100 also includes a light distributor 114 positioned between the subject 110 and the light emitter module 112. The light from the broadband light emitter module 112 is distributed by the light distributor 114. The light distributor 114 may be any suitable mechanism for distributing light, such as, for example, a Fresnel lens or a fiber optic array.

The light-sensing array 106 detects the light 170 transmitted and diffused forward through the subject 110. The light-sensing array 106 may be a two-dimensional light sensor, for example, a camera such as a CCD camera. The light-sensing array 106 serves to record an image of the subject 110 when the light emitter module 112 is activated. A shutter, either mechanical or electronic, serves to gate the light-sensing array 106 with the activation of the light emitter module 112 to reduce interference from ambient light. Alternatively, a narrow band filter may be utilized with the light-sensing array 106 to filter out ambient light, such as light at a wavelength of or shorter than about 600 nanometers.

Figure 3:
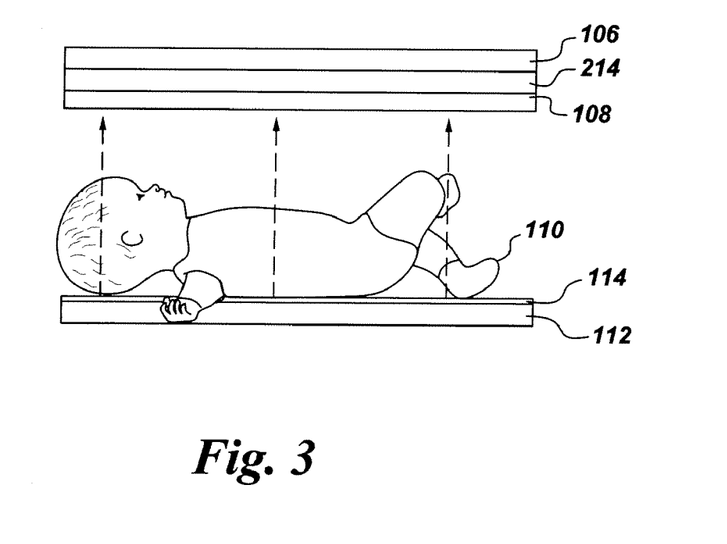
FIG. 3 is a schematic view of a physiological data measurement system constructed in accordance with an embodiment of the invention.

Alternatively, instead of utilizing a broadband light emitter module 112 of the measurement system 100, a light emitter module 212 having multiple wavelengths can be used with a rotary filter wheel 214 positioned adjacent the light-sensing array 106 (FIG. 3). In such an embodiment, the light emitter module 212 includes an optical emitter, such as an LED, for each wavelength to be used in the measurement system. An image is generated for each wavelength source that is activated in the light emitter module 212. In the alternative, wavelength filters may be integrated over pixels in the light-sensing array 106. Optionally, a lens, such as a Fresnel lens, may be placed in front of the light-sensing array 106.

Figure 5A:
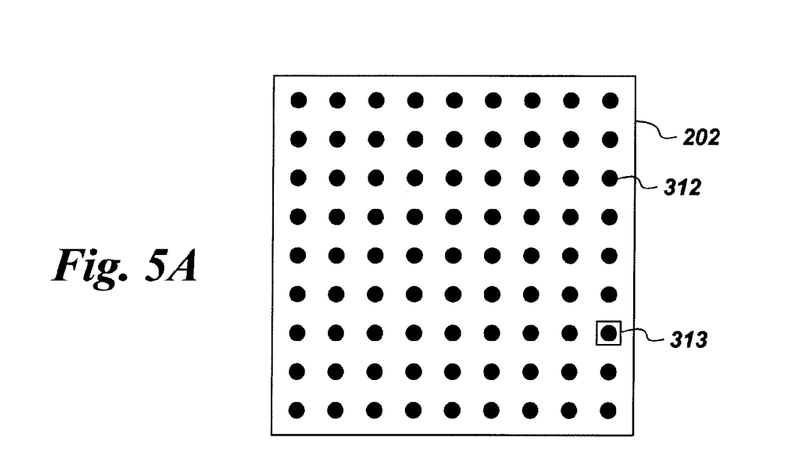
FIG. 5a illustrates the monitoring pad of FIG. 4.
Figure 5B:
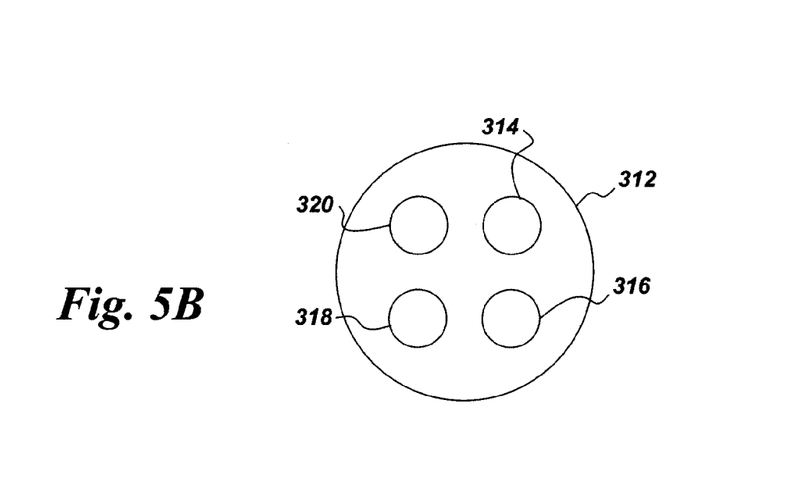
FIG. 5b illustrates the light emitter module of FIG. 4.

Next, as shown in FIGS. 4-5b, is a physiological data measurement system 200 that includes an incubator 150. The measurement system 200 further includes an optical sensor 116 as well as a monitoring mechanism 202. The monitoring mechanism 202, which may include a monitoring pad, has incorporated within a plurality of light emitter modules 312. The light emitter module 312 may be incorporated into flexible circuits, which are multi-layer dielectric systems with conductor wires forming an interconnection array of solid-state optoelectronic semiconductors, such as, for example, vertical cavity surface emitting laser (VCSEL) diodes.

Alternative to incorporating the light emitter modules 312 in the monitoring pad 202, such flexible circuits may be incorporated within and be a part of a conventional heating or thermoelectric cooling pad (not shown). Further, the light emitter modules 312 may instead be incorporated within a fabric that is worn by or draped over or around a subject, such as, for example, a blanket, bed sheets, gown, or robe. The light emitter modules 312 in such a fabric would be an electronically or optically connected arrangement of metal or fiber pads, quantum dots, or nanofibrous electrodes forming leads about the subject 110. Additionally, instead of light emitter modules 312 that employ optical spectra to interrogate the subject as to various physiological data, electromagnetic sensors may be used to obtain electromagnetic field data in such a non-adhering interrogation mechanism.

The light emitter modules 312 may be arrayed in various spatial dispositions, each being positioned beneath an optically transparent surface window 313 that will be oriented normal to the emission path. Only one surface window 313 is schematically shown in FIG. 5a for ease of illustration. It should be appreciated that a surface window 313 corresponds with each light emitter module 312 and can be of any suitable profile. Examples of the various spatial dispositions into which the light emitter modules 312 may be arrayed include, a regularly spaced rectangular grid or Cartesian array (FIG. 5a), a regular array with row-to-row staggering, or an irregularly spaced array with a lower spatial density of light emitter modules 312 in regions of the monitoring pad 202 that are not likely to be beneath a patient 110, such as regions that are more nearly proximate to the pad boundary.

Each of the light emitter modules 312 are individually and repetitively turned on and off according to instructions from the controller 104. A scanner, or other similar mechanism, may be used to activate the light emitter modules 312 in a raster-scan format, completing one scan of all the light emitter modules 312 for each wavelength being used in the measurement system 200. Individual activation of the light emitter modules 312 allows for easy determination as to through what portion of the patient 110 the light is being transmitted and assists in determining an accurate and current position of the patient 110. Repetitive activation of the light emitter modules 312 allows for a greater amount of energy to be transmitted through the body of the patient 110, allowing for greater confidence in the results determined thereby. Activation of the light emitter modules 312 also may be localized to specific regions of the body (for example, the head) to monitor physiological parameters in those areas or for localizing delivery of a therapeutic wavelength.

The light emitter modules 312 are capable of emitting light at two or more wavelengths. Each light emitter module 312 includes an optical emitter, such as, for example, an LED, for each wavelength used in the measurement system 200. As shown in FIG. 4, the light emitter modules 312 emit light 170 at four wavelengths $\lambda_1$, $\lambda_2$, $\lambda_3$, $\lambda_4$. More particularly, and with specific reference to FIG. 5b, each light emitter module 312 includes at least two optical emitters. As illustrated in FIG. 5b, the light emitter module 312 includes four optical emitters 314, 316, 318, 320, each being capable of emitting light 170 at a specific wavelength, such as, respectively, wavelengths $\lambda_1$, $\lambda_2$, $\lambda_3$, $\lambda_4$.

Each of the wavelengths is used in estimating the saturation of hemoglobin. For example, if only two optical emitters 314, 316 are included within each light emitter module 312, one of the optical emitters emits light 170 at wavelength $\lambda_1$, such as a red light, which is used to estimate the patient's blood's oxyhemoglobin saturation, and the other of the optical emitters emits light 170 at wavelength $\lambda_2$, such as an infrared light, which is used to estimate the patient's deoxyhemoglobin level. The beams of red and infrared light are transmitted through a pulsating capillary bed within the patient 110. The ratio of red to infrared blood light transmitted gives a measure of the oxygen saturation of the blood. An addition of two more optical emitters 318, 320, each emitting light at a different wavelength $\lambda_3$, $\lambda_4$, allows for the estimation of the patient's blood's carboxyhemoglobin and methemoglobin conditions.

The optical emitters 314, 316, 318, 320 may be any suitable light emitting mechanism, such as, for example, VCSELs, a type of semiconductor laser with a laser beam emission that is perpendicular to the chip surface. Alternatively, the optical emitters 314, 316, 318, 320 may include optical conduits for VCSELs recessed below the surface of monitoring pad 202. The optical emitters 314, 316, 318, 320 may be made to diffuse the emitted light 170 and, in one embodiment, may be made to approximate a Lambertian radiator. Other suitable light emitting mechanisms include tunable lasers. Suitable lasers may be oriented to emit light in a direction perpendicular to the optically transparent surface window 313 of the monitoring pad 202 and properly collimated to transmit through a subject and, if necessary, through an incubator environment.

Neonatal patients 110, due to their small size, are relatively transparent, especially in certain body regions, to emitted light 170. Generally, neonates are placed within an incubator 150 without any clothing, and only a small diaper. Other, larger patients 110 are less transparent to emitted light 170 than neonates. Further, other larger patients usually are covered with a hospital gown and may also be covered with bed sheets and/or blankets. Conventional hospital gowns and bed sheets/blankets may not be transparent to emitted light 170. Clothing the patients 110 in gowns and bed sheets/blankets that are transparent to emitted light 170 would allow use of the measurement system 200 during a surgical procedure. Further, the measurement system 200 can be used for monitoring the patient 110 in his bed by placing the monitoring pad 202 on the bed and incorporating an optical sensor 116 as described in reference to FIG. 4.

Figure 6:
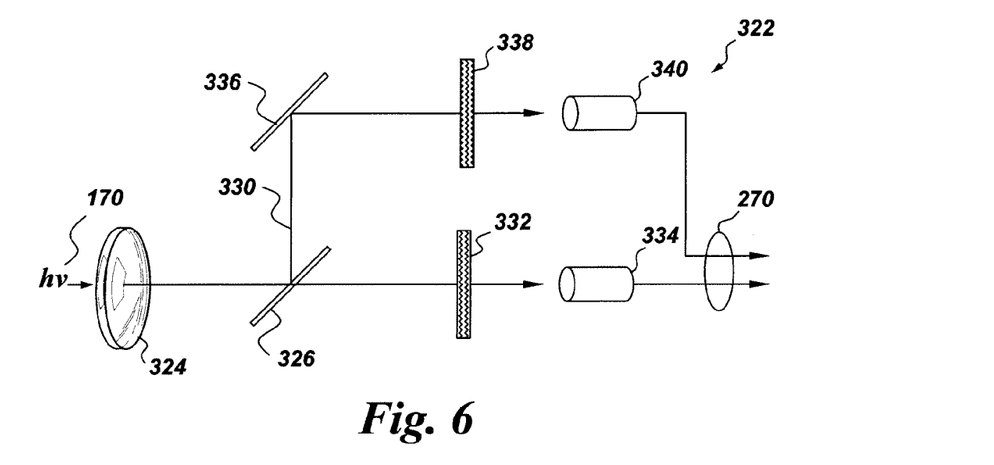
FIG. 6 illustrates the optical sensor of FIG. 4.

With specific reference to FIG. 6, next will be described one embodiment of an optical sensor 322 that is configured to measure two wavelengths of emitted light 170. Electronic equipment, used to process signals from the optical sensor 322, serves to generate an image for each wavelength. The image is then processed for each pixel to determine the hemoglobin levels corresponding to each light emitter module 312. A light-collecting lens is used to gather light over a wide area and concentrate that light on the optical sensor 322. The light-collector lens may be, for example, a Fresnel lens to reduce the size of the apparatus.

The emitted light 170 is received by the optical sensor 322 and collimated by a lens 324. If the emitted light 170 is transmitted from a broadband light emitter module, then the collimated light is passed to a beam splitter 326, which splits the collimated light into a first beam 328 and a second beam 330. Instead of a beam splitter, a rotating filter wheel may alternatively be used to obtain sequential images from optical sensor 322 at different wavelengths. The first beam 328 is passed into an optical wavelength band pass filter 332, which has a band pass centered on a particular wavelength, such as wavelength $\lambda_1$. Light within the wavelength $\lambda_1$ is transmitted to a first detector 334. The second beam 330 is passed into an optical wavelength band pass filter 338, which has a band pass centered on a second particular wavelength, such as wavelength $\lambda_2$. Optionally, and as shown, a mirror 336 may be incorporated between the beam splitter 326 and the optical wavelength band pass filter 338. Light within the wavelength $\lambda_2$ is transmitted to a second detector 340. If the emitted light 170 is transmitted from the array of light emitter modules 312, the beam splitter 326 becomes unnecessary. Instead, the different wavelengths are distinguished by illuminating one wavelength at a time.

Output 270 from the detectors 334, 340 is sent to the controller 104 via a communications path 160. The communications path 160 may include any suitable communications medium, such as, for example, free space optical communications means like infrared, RF wireless, electrical cable, or optical fiber. It should be appreciated that if the emitted light 170 contains light with more than two wavelengths, such as four wavelengths $\lambda_1$, $\lambda_2$, $\lambda_3$, $\lambda_4$, the optical sensor 322 can be expanded to provide four band pass filters and four detectors.

Figure 7:
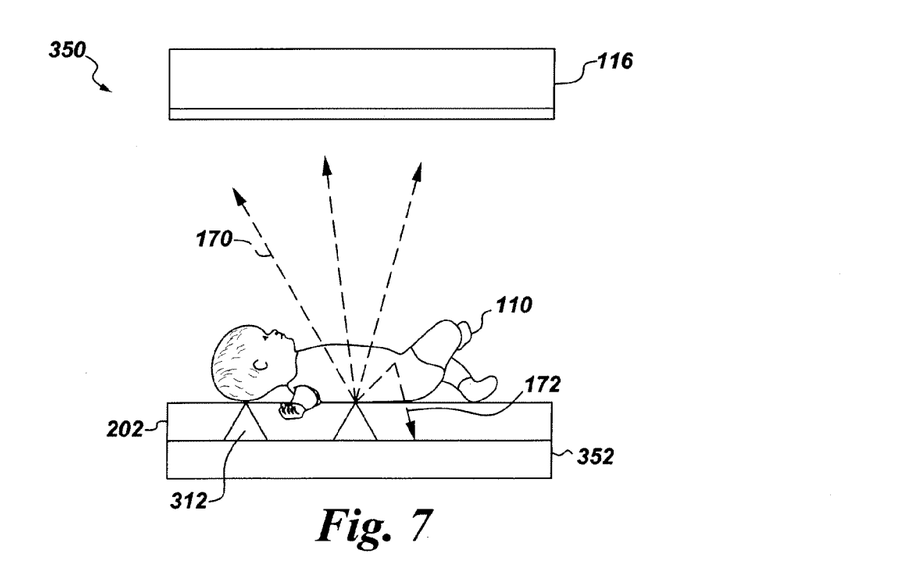
FIG. 7 is a schematic view of a physiological data measurement system constructed in accordance with another embodiment of the invention.

Although the embodiments described with reference to FIGS. 2-4 have included a monitoring pad beneath the subject patient 110 and capable of transmitting light into the patient and diffusing the light forward to an overhead optical sensor, it should be appreciated that the invention is not so limited. Any arrangement that allows light to be emitted from within or on a monitoring pad and into a subject patient 110 is within the scope of the invention. For example, and with specific reference to FIG. 7, a physiological data measurement system 350 is shown including the monitoring pad 202 and the optical sensor 116, but also including a second optical sensor 352 co-located with the pad 202. The light emitter modules 312 located within the monitoring pad 202 emit light 170 that is transmitted through the body of the subject patient 110 and diffused forward to be received at the optical sensor 116. Further, some of the light 170 is transmitted into the body of the subject patient 110 and diffused back as reflected light 172 to be received at the second optical sensor 352. It should be appreciated that a suitable measurement system may include the optical sensor 116, the optical sensor 352, or both.

Alternatively, for neonate subjects 110, the incubator 150 may utilize multiple optical transmitters, such as VCSELs or LEDs, on an overhead shell surface. Such an incubator 150 may have a base layer underneath the subject 110 that includes a networked surface for communication, control and power. Power on the networked surface may be provided in ultra-low direct current voltage and include current limiting hardware. The overhead shell would remain optically clear and include VCSELs or LEDs and power conductors. The longer wavelength, near-infrared light penetrates tissues deeper than visible light, allowing transmission through a subject 110. Such light is also preferably pulsed, thus inhibiting tissue heating.

Figure 8:
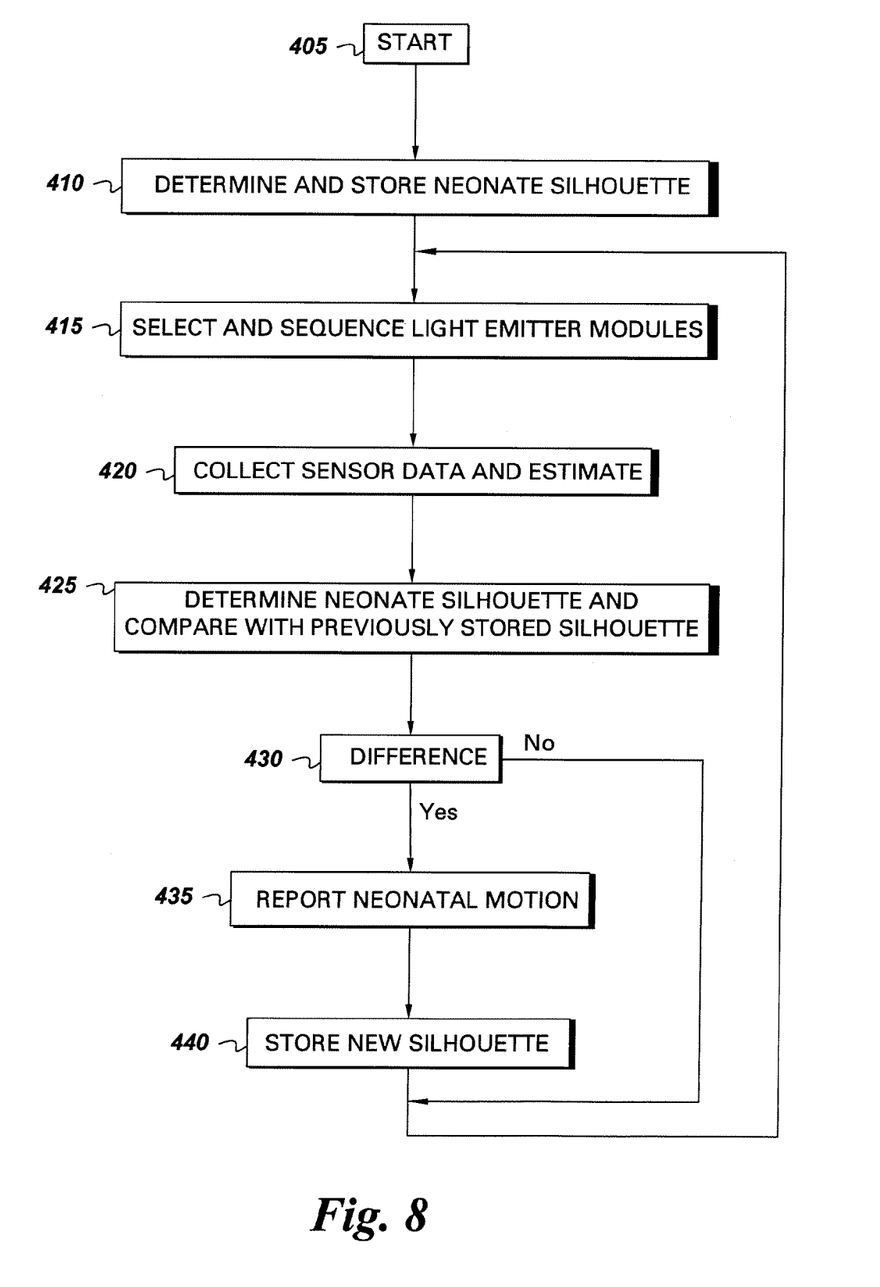
FIG. 8 illustrates process steps for using the physiological data measurement system of FIG. 4 in accordance with another embodiment of the invention.

Referring now to FIG. 8, next will be described a process for obtaining physiological data measurement from a patient 110. At Step 405, the process is initialized. During the initialization step, the patient 110 is placed on the monitoring pad. For a patient 110 that is a neonate, that encompasses placing the neonate within the incubator 150 (FIG. 4) and upon the monitoring pad. At Step 410, the outline of the patient 110, or the patient's silhouette, is determined and stored within the controller 104. One method of determining the patient's silhouette is to turn every light emitter module on and off sequentially. If the optical sensor detects a level of light 170 indicative of an unobstructed line of sight from a particular light emitter module to the sensor, than the position of that light emitter module is determined to be outside of the patient's silhouette. Conversely, if the level of light 170 is indicative of an obstructed line of sight, than the position of the light emitter module is determined to be within the patient's silhouette.

Next, at Step 415, the controller 104 selects light emitter modules within select regions of interest within the patient's silhouette and turns each of the selected light emitter modules in each region of interest on and off. The light emitter modules may be individually turned on and off, region by region. For example, if the regions of interest include the center of the head, part of the thoracic area, and part of the safenous area, the light emitter modules corresponding to those three regions would be turned on, individually, in one region (for example the head), followed by the second region (thoracic area), and then the third region (safenous area).

Sensor data is collected at Step 420 and physiological data values are estimated. The sensor data collected includes the sequential region illuminations of the patient 110, and this data is used to estimate physiological data values. This data is then logged. At Step 425, the outline of the patient 110 is again determined, and this second outline is compared with the previously determined outline. A difference in the outlines signifies movement of the patient 110. At Step 430, a determination is made whether there is a difference in the silhouettes of the patient 110. If there is no change in the silhouettes, the process can move back to Step 415. Conversely, if there is a determined change in the silhouettes, a report is generated at Step 435 of movement by the patient 110. Finally, at Step 440, the new silhouette is stored, replacing the previously stored silhouette, and the process moves back to Step 415.

While the measurement system embodiments have been described and shown for the application of obtaining physiological data through a non-adhering interrogation mechanism, it should be appreciated that the same embodiments may be utilized for a different purpose. For example, such a non-adhering interrogation mechanism may include light emitters that emit light at a therapeutic wavelength that, for example, may enable the activation of light-sensitive chemotherapy drugs (photodynamic therapy). Such photodynamic therapy may be used, for example, for the destruction of cancer. Alternatively, such a non-adhering interrogation mechanism may be used to introduce light at a therapeutic wavelength to react with cytochromes in cells of the subject 110 that respond to light and color to stimulate tissue growth and regeneration. In such treatment systems, the monitoring mechanism would instead function as an optical treatment array mechanism. Another such photodynamic therapy may include the shining of a fluorescent light on a neonate for the treatment of hyperbiliruben.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A physiological data measurement system adapted to monitor a subject, comprising:
   a non-intrusive signal emitting mechanism, comprising:
      a monitoring mechanism configured to monitor physiological data of and provide support to the subject while the subject is being monitored; and
      at least one signal emitter module within the monitoring mechanism;

a signal receiving mechanism configured to receive signals emitted from said at least one signal emitter module; and a controller configured to control said at least one signal emitter module based at least in part on a determined position of the subject being monitored on the monitoring mechanism.

2. The measurement system of claim 1, wherein the physiological data is oximetric data.

3. The measurement system of claim 1, wherein said signal receiving mechanism comprises a plurality of electromagnetic sensors.

4. The measurement system of claim 1, wherein said at least one signal emitter module comprises one or more light emitter modules.

5. The measurement system of claim 4, wherein said one or more light emitter modules comprises a plurality of optical emitters, each configured to emit light at a different wavelength from the others.

6. The measurement system of claim 5, wherein each said optical emitter comprises a VCSEL.

7. The measurement system of claim 5, wherein each said optical emitter comprises a LED.

8. The measurement system of claim 4, wherein said signal receiving mechanism comprises an optical sensor.

9. The measurement system of claim 8, wherein said optical sensor comprises a CCD camera.

10. The measurement system of claim 8, further comprising a light distributor positioned between a single one of said one or more light emitter modules and said optical sensor.

11. The measurement system of claim 10, wherein said single one of said one or more light emitter modules comprises an optical emitter configured to emit light at a plurality of wavelengths.

12. The measurement system of claim 11, wherein said optical emitter comprises a broadband light source.

13. The measurement system of claim 12, further comprising:

a lens;

a rotating filter wheel;

a plurality of band pass filters; and a detector.

14. The measurement system of claim 8, wherein said optical sensor comprises:

a lens;

a beam splitter;

first and second band pass filters, said first band pass filter having a band pass centered on a first wavelength and said second band pass filter having a band pass centered on a second wavelength; and first and second detectors, said first detector configured to receive light of the first wavelength from said first band pass filter and said second detector configured to receive light of the second wavelength from said second band pass filter.

15. The measurement system of claim 8, wherein said optical sensor is positioned such that light emitted from the one or more light emitter modules is transmitted into a subject and diffused forward prior to being received at said optical sensor.

16. The measurement system of claim 8, wherein said optical sensor is positioned such that light emitted from the one or more light emitting modules is transmitted into a subject and diffused back to be received at said optical sensor.

17. The measurement system of claim 8, further comprising a second optical sensor.

18. The measurement system of claim 8, wherein said optical sensor comprises a two-dimensional light sensor.

19. The measurement system of claim 1, wherein said monitoring mechanism comprises a pad incorporating said at least one signal emitter module.

20. The measurement system of claim 1, wherein said monitoring mechanism comprises a fabric incorporating said at least one signal emitter module.

* * * * *